United States Patent
West, Jr. et al.

[11] Patent Number: 5,964,764
[45] Date of Patent: Oct. 12, 1999

[54] APPARATUS AND METHODS FOR MOUNTING A LIGAMENT GRAFT TO A BONE

[75] Inventors: Hugh S. West, Jr., 1373 E. Harvard Ave., Salt Lake City, Utah 84105; John R. West, Salt Lake City, Utah

[73] Assignee: Hugh S. West, Jr., Salt Lake City, Utah

[21] Appl. No.: 09/046,988

[22] Filed: Mar. 24, 1998

[51] Int. Cl.⁶ .................................................. A61B 17/56
[52] U.S. Cl. ................................ 606/72; 606/73; 606/75; 623/13; 623/15; 623/17
[58] Field of Search ................................. 606/72, 73, 74, 606/75, 64–65, 104, 105, 232; 623/13–15, 17, 22, 23

[56] References Cited

U.S. PATENT DOCUMENTS

| | | | |
|---|---|---|---|
| 2,563,164 | 8/1951 | Fletcher et al. | 294/89 |
| 4,447,182 | 5/1984 | Murbach | 411/45 |
| 4,643,734 | 2/1987 | Lin | 623/16 |
| 4,738,255 | 4/1988 | Goble et al. | 128/92 |
| 4,772,286 | 9/1988 | Goble et al. | 623/13 |
| 4,778,468 | 10/1988 | Hung et al. | 623/16 |
| 4,834,752 | 5/1989 | Van Kampen | 623/13 |
| 4,906,148 | 3/1990 | Schule | 411/34 |
| 4,997,433 | 3/1991 | Goble et al. | 606/64 |
| 5,004,474 | 4/1991 | Fronk et al. | 623/13 |
| 5,078,745 | 1/1992 | Rhenter et al. | 623/13 |
| 5,139,520 | 8/1992 | Rosenberg | 623/13 |
| 5,151,104 | 9/1992 | Kenna | 606/73 |
| 5,152,790 | 10/1992 | Rosenberg et al. | 623/13 |
| 5,203,784 | 4/1993 | Ross et al. | 606/104 |
| 5,228,815 | 7/1993 | Gignac et al. | 411/45 |
| 5,266,075 | 11/1993 | Clark et al. | 623/15 |
| 5,356,413 | 10/1994 | Martins et al. | 606/232 |
| 5,356,435 | 10/1994 | Thein | 623/15 |
| 5,374,269 | 12/1994 | Rosenberg | 606/80 |
| 5,393,302 | 2/1995 | Clark et al. | 623/13 |
| 5,397,357 | 3/1995 | Schmeiding et al. | 623/13 |
| 5,456,721 | 10/1995 | Legrand | 623/13 |
| 5,505,735 | 4/1996 | Li | 606/232 |
| 5,556,428 | 9/1996 | Shah | 623/13 |
| 5,560,669 | 10/1996 | Gute | 296/97.9 |
| 5,575,819 | 11/1996 | Amis | 623/13 |
| 5,632,748 | 5/1997 | Beck, Jr. et al. | 606/89 |

FOREIGN PATENT DOCUMENTS

| | | | |
|---|---|---|---|
| 0 145 492 | 6/1985 | European Pat. Off. . | |
| WO 92016167 | 10/1992 | WIPO | 623/13 |

*Primary Examiner*—Michael Buiz
*Assistant Examiner*—Lien Ngo
*Attorney, Agent, or Firm*—Workman, Nydegger & Seeley; John M. Guynn

[57] ABSTRACT

An anchor device for mounting a bodily tissue to a bone, such as for repairing ligaments and tendons, particularly ham string tissue grafts for repairing a knee joint. The anchor device is configured and sized to pass through a bone tunnel and comprises a sheath member having a bone-engagement end and bodily tissue attachment end. The bone-engagement end includes structure for selective overlapping and engaging the bone adjacent an exit opening of the bone tunnel. The bodily tissue attachment end includes structure known in the art for attaching a bodily tissue, such as a ligament, tendon, or ligament graft, to the sheath member. The anchor device further includes a camming member slidably disposed relative to the sheath member, which selectively urges the sheath member to engage the bone surface. The sheath member and camming member include interlocking features for locking the anchor device in a deployed position within the bond tunnel. The anchor device also includes structures which give the surgeon a tactile, aural or other indication when the anchor device has been deployed and locked in the deployed position. The anchor device is preferably inserted, deployed and locked by means of a system of suture cords in order to reduce the number of incisions necessary to anchor the bodily tissue to the bone.

40 Claims, 7 Drawing Sheets

APPARATUS AND METHODS FOR MOUNTING A LIGAMENT GRAFT TO A BONE

BACKGROUND OF THE INVENTION

1. The Field of the Invention

The present invention is in the field of devices for attaching bodily tissue to a bone. More specifically, the present invention is directed to an anchor device for attaching an end of a bodily tissue, such as a tendon, ligament or replacement graft ligament under tension to a bone for repairing or replacing a damaged tendon or ligament.

2. The Relevant Technology

Damaged tissues, such as torn or ruptured ligaments, are commonly replaced by grafts from other replacement tissues such as tendons, muscles or artificial materials. While medical techniques in replacing damaged ligaments have greatly advanced over the past few years, one problem with presently used ligament replacement and repairing techniques is the need to provide a firm and reliable fixation point for the graft replacement tissue.

In ligament replacement surgical procedures, particularly in cruciate ligament reconstruction procedures for an injured knee, a graft ligament tunnel is usually formed through bones on both sides of the joint being repaired. A replacement ligament graft is then passed through the pre-formed tunnels of both bones until the replacement ligament graft extends through both bones. Both ends of the ligament graft are then secured to the bones under tension across the joint in order to tie the two bones together in a manner that mimics the torn or broken ligament being repaired or replaced.

In the past, ligaments have been secured to the bones by means of surgical stables, screws or buttons. A problem with using staples and conventional buttons to attach both ends of a ligament graft to a bone is that both require two incisions. Once in place, staples are not easily removed in the case where adjustments are necessary. Staple removal could subject the bone to undue trauma and even result in mutilation of the bone. In addition, the graft ligament can sometimes slip out from under the staple by working its way loose. While buttons tend to be easier to remove in the case where adjustments are necessary, adjustments thereto requires severing or untying of the cords or sutures securing the ligament graft to the button and then retying of the sutures.

A variation of the surgical button known as an "ENDOBUTTON" can be used in a manner that allows for a single incision to made. The ENDOBUTTON consists of a small beam-like elongated button that can be inserted through a bone tunnel using sutures rather than a second incision, which is an improvement over ordinary surgical buttons in this regard. However, ENDOBUTTONS, like all buttons, require a suture link with the tendon or ligament graft, which provides for a more flexible and elastic linkage between the bone and tissue graft. The knot in the suture used to attach the tissue graft and ENDOBUTTON requires a knot, which introduces a certain level of risk of failure and requires proper tying to avoid risk of knot failure. Moreover, the inherent elasticity of a suture linkage results in a less rigid and secure linkage, which can decrease the ability of the tissue graft to form a strong biological adhesion or fusion with the bone tunnel. This can have both short-term and long-term negative consequences.

Finally, endosteal interference screws have the limitation of being attached to soft interior bone rather than the hard cortical bone surface. In addition, interference screws provide a considerably smaller surface area within the bone hole for biological healing and attachment of the ligament graft. This is because interference screw tends to push the ligament graft to one side of the hole, with the majority of volume within the hole being occupied by the screw. This can result in a less secure biological bond compared to other securement methods that allow for the ligament graft to make contact with more of the bone hole surface. Since the quality of bone in the tunnel is highly variable, the standard deviation of pullout strength is greatly increased in the case where interference screws are employed.

Many other procedures and devices have been developed for attaching a replacement ligament graft to bone. However, many have not proven adequate and have raised serious issues with respect to the strength, stiffness, and reliability of the ligament graft. Each of these raise important issues as to the clinical success of the procedure. In addition, many of the more innovative devices and procedures require complicated tooling.

U.S. Pat. No. 4,997,433 to Goble et al. discloses an alternative anchor device for mounting a ligament within a bone tunnel under tension. The Goble et al. device consists of a pair of stud arms defining a space at the rearward end for longitudinal receipt of a ligament end and a cylindrical stud having a hook edge at a forward end. The ligament is secured between the stud arms by means of screws, preferably in combination with a bone plug that acts as a stiffening aid. A major problem with the stud arms is that they are interposed between the ligament graft and the bone tunnel, which diminishes the overall surface area contact between the ligament graft and bone tunnel wall. This results in a substantial reduction of the tendency to form a biological bond over a large surface area of the graft ligament and the bone tunnel wall, thus compromising the long term strength and stability of the graft.

The forward end having the hook edge is compressible due to a longitudinal slot running therethrough, which allows the hook edge to be flexed or compressed inwardly against a spring-like resistance to allow for passage through a ligament tunnel. The Goble et al. device is installed by pulling the stud connected to the ligament end through the ligament tunnel, with the angled top of the hook edge acting as a camming surface that causes the hook end to compress inwardly to allow passage through the ligament tunnel. Because of the spring-like resilience of the Goble et al. device, the forward end springs outwardly back to its uncompressed state as the hook end emerges from the ligament tunnel, which causes the hook end to extend over and engage the bone cortex.

Because the forward end requires sufficient spreading force to reliably ensure that the hook end is, in fact, forced to expand outwardly by its own internal spring-driven power without any external mechanical assistance, the hook end is necessarily caused to push with substantial force against the ligament tunnel wall. Hence, although Goble et al. purports to teach the use of sutures to deploy the Goble et al. stud, in practice a threaded tool that screws into a corresponding threaded female portion of the Goble et al. stud is required to apply the force necessary to reliably force the device through the ligament tunnel. Use of this special tool adds an additional level of invasiveness and difficulty into the procedure.

In view of the foregoing, there exists a need for a simple, more easily deployed anchor device that could securely attach a bodily tissue such as a replacement ligament graft to a bone.

It would be an additional improvement in the art if such anchor device could be reliably deployed while minimizing the invasiveness of the surgery, particularly the number of incisions that would have to be made to deploy the anchor device.

In addition, it would be an advancement in the art to provide an improved anchor device that included a mechanism that provided a discernable signal or means to indicate when the anchor device has been successfully deployed and securely engaged within the bone.

It would be a further improvement in the art to provide an anchor device that allowed for broad surface contact between the graft tissue and the inner surface of the bone tunnel in order to increase the biological bond and provide a stronger, more reliable connection with the bone.

It would yet be an improvement in the art if such anchor device could be easily molded from a bio-absorbable material.

Such anchor devices for reliably and securely mounting bodily tissues such as ligaments and tendons to a bone are disclosed and claimed herein.

SUMMARY AND OBJECTS OF THE INVENTION

The present invention is directed to an anchor device for repairing, reattaching or replacing a bodily tissue such as a tendon, ligament, or replacement ligament graft to a bone. The inventive anchor device can be deployed to connect a ligament graft, particular a ham string tissue graft, within a bone tunnel with only a single incision. It includes features that safely, securely and reliably engage the bone to form a reliable and rigid connection between the tissue graft and the bone in the short term, and which also promotes good biological fusion between the graft and the bone for long term stability. The device includes a deployment mechanism that allows the surgeon to reliably deploy and lock the anchor device and also determine when the anchor device has been properly deployed and locked without the use of special tools.

As used herein, the term "anchor device" is defined as a system or apparatus that can be used to attach, anchor, bind, connect, fasten, secure, mount or otherwise affix a bodily tissue such as a tendon, ligament or graft ligament within a bone tunnel.

As used herein, the term "bodily tissue" is defined as any tissue in the body that may require attachment to a bone or other surface in the body, such as a ligament, tendon, graft ligament, cartilage, or other tissue graft, which may be either natural, artificial or a combination of natural and artificial tissue.

As used herein, the term "deploy" is defined as the process or steps by which the anchor device is inserted through a bone tunnel and manipulated so that bone-engagement structure of the anchor device is caused to overlap cortical bone around the exit end of the bone tunnel.

As used herein, the term "lock" is defined as the process or steps by which features within the anchor device mechanically interlock to maintain the anchor device in the deployed condition and prevent unwanted pullout of the anchor device back through the bone tunnel after deployment.

As used herein, the term "signal" is define as the sound, feel, or other indication heard, felt, or otherwise detected by the surgeon that gives the assurance that the anchor device has been both properly deployed and locked into the deployed state.

The anchor device, according to the present invention, generally comprises a sheath member having a flexible bone-engagement end that includes at least one bone-engagement lip for engaging the outer surface of a bone. The sheath member also includes a graft tissue attachment end that includes means for attaching a bodily tissue to the sheath member. The bone-engagement end of the sheath member is configured to first allow the bone-engagement lip to be retracted inwardly while passing through a bone tunnel during deployment and thereafter expand outwardly during final deployment. Retraction of the lip inwardly allows the bone-engagement end to have a sufficiently reduced diameter in order for the anchor device to fit through a pre-formed bone tunnel. Outward expansion of the bone-engagement lip allows the lip to overlap the cortical bone surface in order to securely and reliably engage the outer bone surface. This secures the anchor device within the bone in a manner that prevents pull-out of the device from the bone tunnel so long as the bone-engagement lip reliably overlaps the bone surface.

The anchor device further comprises a slidable cam member that works in combination with the sheath member to deploy the anchor device and thereby mechanically urge the bone-engagement lip to expand or move outwardly to ensure adequate mechanical overlap with the bone surface surrounding the exit end of the bone tunnel. The cam member preferably also serves the purpose of maintaining the bone-engagement lip in an expanded and deployed state after insertion and deployment of the anchor device. The camming feature thereby provides means for spreading, bending or otherwise expanding the bone-engagement end of the sheath member to cause the bone-engagement lip to overlap the bone surface. It also preferably serves as means for maintaining the bone-engagement lip in the deployed state.

The cam member and sheath member preferably include interlocking features that allow for the cam member and sheath member to lock together and be fixed in a relatively immovable position relative to each other upon deploying the anchor device. This prevents the cam member from inadvertently slipping out of the deployed position, which, in turn, reliably maintains the bone-engagement lip in a securely deployed configuration. As such, the interlocking features work together to prevent the anchor device from experiencing unwanted pullout after deployment. The interlocking features preferably include at least one ridge within either or both of the cam member and sheath member configured to mate with a corresponding groove in the other of the cam member or sheath member upon deployment. The camming action of the cam member not only maintains the bone-engagement lip in the deployed state, but also helps to reliably maintain engagement between the ridge and corresponding recess.

The anchor device preferably includes lock signaling means for indicating to the surgeon when the anchor device has been successfully deployed and that the sheath member and cam member have been securely locked together as described above. The signaling means may be provided by the aforementioned ridge and corresponding groove comprising the locking mechanism, which are advantageously configured to provide a snap-fit engagement that can be heard, felt, or otherwise reliably detected by the operating surgeon. Of course, other mechanical features in addition to, or instead of, the mechanically interlocking lock features may provide the signalling means. Electronic detection and signaling features may be provided so long as they do not interfere with the ligament attaching procedure. However, the signaling means may be as simple as a suture having a visible marking that is attached to the camming means and which allows for visual monitoring of relative movement between the camming means and the sheath means during deployment.

In addition to the foregoing features, the anchor device preferably includes a substantially cylindrical extension that projects longitudinally from the attachment end. The purpose of the extension is to aid in pushing or urging the tissue graft radially against the circumferential inner wall of the bone tunnel. This provides a more intimate contact between the tissue graft and the bone tunnel wall over a greater surface area, which promotes both earlier fixation as well as a more secure long-term biological attachment between the graft bodily tissue and the bone.

In a preferred method of deployment, the anchor device comprising the sheath member and the slidable member in a non-deployed state are inserted through a pre-prepared bone tunnel and then deployed to cause overlap of the bone-engagement lip and the surrounding bone surface. Insertion and deployment of the anchor device are preferably carried out by means of a system of suture strings or cords strategically placed within the anchor device. The suture strings or cords should be sufficiently strong so that they will not break during deployment, but which can be easily cut and removed as desired after successful and complete deployment of the anchor device. The suture strings provide for minimal invasiveness since they are typically very narrow and flexible.

In use, a bodily tissue is attached to the bodily tissue attachment end of the sheath member, preferably by looping one or more strands of the bodily tissue through a loop portion of the sheath member. The anchor device and attached the bodily tissue are then maneuvered through the insertion side of a pre-formed bone tunnel by means of one or more suture cords. In the non-deployed state, the sheath member assumes a conformation that gives it a narrower diameter than the bone tunnel to allow the bone-engagement lip to pass through and not snag or bind within the bone tunnel. After the surgeon determines that the bone-engagement end of the sheath member has emerged from the exit opening of the bone tunnel, the slidable member is moved relative to the sheath member in order to cause the camming structure to urge the bone-engagement lip to spread outwardly and thereby overlap the bone surface outside the bone tunnel. The interlocking features are preferably engaged upon successful deployment of the bone-engagement lip to retain the lip in the desired bone-overlapping position. In addition, the interlocking features preferably snap together while in the process of locking the sheath member and slidable member together in order to provide a positive tactile indication to the surgeon that the anchor device has securely deployed and locked within the bone tunnel. The anchor device can optionally include a disengagement feature for allowing de-deployment of the anchor device even after having been deployed and locked.

Typically, the end of the bodily tissue opposite the end attached to the anchor device is attached after attaching the anchor device as described herein. Preferably, the bodily tissue is attached in a manner that provides tension on the anchor device in order to securely maintain the anchor device and bodily tissue within the bone tunnel in a relatively fixed and rigid position to promote good biological adhesion between the bodily tissue and the bone.

In a preferred embodiment, the sheath member is molded or otherwise manufactured in a manner that causes the bone-engagement lip to assume a normally compressed or non-deployed conformation. This allows for the anchor device to be more easily inserted through the bone tunnel and aids in preventing unwanted friction or mechanical binding between the lip and the inner wall of the bone tunnel. Nevertheless, the sheath member can also be manufactured so that the bone-engagement lip has a normally expanded conformation. This may be advantageous, for example, in the case where the anchor device include means for de-deployment of the anchor device after deployment and locking.

In view of the foregoing, it is an object of the present invention to provide a simple, more easily deployed anchor device that can securely attach a bodily tissue such as a replacement ligament graft to a bone.

It is an additional object and feature of the present invention to provide an anchor device that can be reliably deployed while minimizing the invasiveness of the surgery, particularly the number of incisions that have to be made by the surgeon for proper deployment.

Moreover, it is an object to provide an anchor device that includes a mechanism that provides a discernable signal or means to indicate when the anchor device has been successfully deployed and securely engaged within the bone.

It is yet an object of the present invention to provide an anchor device that allows for broad surface contact between the graft tissue and the inner surface of the bone tunnel in order increase the biological bond and provide a stronger, more reliable connection with the bone.

Furthermore, it is an object and feature of the present invention to provide an anchor device that can be easily molded from a bio-absorbable material.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is directed to an anchor device for repairing, reattaching or replacing a bodily tissue such as a tendon, ligament, or replacement ligament graft to a bone. In addition, preferred methods for using the inventive anchor device are also disclosed. The inventive anchor device can be deployed to connect a bodily tissue to a bone using only a single incision, particularly a ham string tissue graft for repairing a knee joint. The anchor device includes features that securely engage the bone to form a reliable and rigid connection between the bodily tissue graft and the bone, which promotes good biological fusion between the graft and the bone for long term stability. The anchor device includes a deployment mechanism that allows the surgeon to reliably determine when the anchor device has been properly deployed without the use of special tools.

The anchor device comprises a sheath member and a cam member slidably disposed relative to the sheath member. The sheath member further includes means for attaching a bodily tissue to one end and means disposed at an opposite end for overlapping and engaging the outer surface of a bone through which the anchor device has been deployed. The cam member preferably has a slidable mechanical relationship to the sheath member, which allows the cam member to be moved into a deployed position by means of one or more deployment sutures. Using a system of insertion and deployment sutures to first insert and then deploy the anchor device obviates the need for special insertion and deployment tools, which greatly reduces the invasiveness of the bodily tissue attachment procedure.

The sheath member and cam member are preferably configured to include interlocking mechanical features with lock or substantially secure the sheath member relative to the cam member in order to lock the anchor device in the deployed condition. Such interlocking mechanical features are advantageously configured to provide signaling means for confirming to the surgeon that the anchor device has been properly deployed and locked in the deployed position within the bone tunnel.

The interlocking mechanical features preferably comprise a complementary ridge and recess which mate to provide a snap-fit engagement upon sliding the cam member into a locked position relative to the sheath member. The snap-fit engagement of the ridge and recess creates a tactile sensation, an audible click, and/or other mechanical sensation which can be detected by the operating surgeon, which will confirm that the anchor device has been properly deployed and locked. After confirmation of secure deployment and locking of the anchor device, the insertion and deployment sutures can be removed by simply severing and then removing the sutures from the anchor device and surgery site.

The means within the sheath member for overlapping and engaging the cortical surface of a bone may comprise any appropriate structure that can maintain the sheath member in a relatively rigid position upon deployment. A preferred structure is a single bone-engagement lip extending laterally from the bone-engagement end of the sheath. The lip may have any appropriate angle relative to the axis of the sheath, which can be selected based on a number of factors, such as the angle of the bone tunnel relative to the bone axis or the amount of desired "bite" of the lip into the bone surface versus the amount of desired flat surface contact between the lip and the bone surface. The length of the bone-engagement lip may also be adjusted as desired in order to optimize the ease of insertion through the bone tunnel versus the strength of the engagement with the bone surface upon deployment. Shorter lips tend to facilitate insertion through the bone tunnel while longer lips tend to provide a stronger mechanical overlap with the bone surface, since there will be more surface contact with the bone to provide resistance to pull-out. Double-lipped sheaths are an alternative embodiment of bone-overlapping and engaging means.

As will be seen below in the drawings, a preferred configuration provides for the cam member to be attached to a pin member that slidably fits within the interior of the sheath member. The corresponding sheath member is preferably molded in order to assume a normally compressed and non-deployed conformation while in a relaxed state, which causes the bone-engagement lip to normally assume a non-deployed and withdrawn position to facilitate entry of the anchor device through the bone tunnel. After the bone-engagement end of the sheath member has emerged through the exit end of the bone tunnel, the pin member is slidably withdrawn into the interior of the sheath member. A cam structure on the pin member urges the bone-engagement lip of the sheath member to extend over the bone surface as the pin member is withdrawn into the sheath member.

In an alternative embodiment, the cam member may comprise a sliding wedge member or other mechanical feature that is slidably disposed adjacent the bone-engagement end of the sheath member. In a sliding wedge configuration, the anchor device is in a non-deployed and unlocked condition when the narrower portion of the slidable wedge member is adjacent to the bone-engagement end of the sheath member. It is in a deployed and locked configuration when the wedge member is positioned such that the wider portion is adjacent to the bone-engagement end. As the width of the wedge member adjacent the bone-engagement end increases, the bone-engagement lip is forced to deflect outwardly with respect to the bone tunnel and overlap a portion of the surrounding bone surface.

The anchor device optionally includes means for increasing the interface between the graft bodily tissue and the bone tunnel surface. Such interface increasing means preferably includes a substantially cylindrical extension that projects longitudinally from the attachment end of the sheath member. The extension works by radially displacing the bodily tissue graft from the center of the bone tunnel outwardly against the circumferential wall of the bone tunnel. This provides a more positive and uniform contact between the bodily tissue graft and the bone tunnel wall, which promotes early fixation as well as stronger long-term biological attachment between the graft bodily tissue and the bone. Of course, the extension need not be cylindrical but can be any shape so long as it provides the intended function of increasing the area of surface contact between the bodily tissue graft and the bone tunnel.

In the discussion that follows is a detailed description of illustrative embodiments of the present invention depicted in the drawings. The specific mechanical features that are depicted and that will be discussed hereinafter in detail are intended to be illustrative of the functions which they have been designed to perform. To the extent that such features may provide other functions not expressly described herein but which are inherent or obvious to one of ordinary skill, such other non-specified functions are to be considered to be part of this invention. In addition, while illustrative mechanical and design features are depicted in the drawings, other design features not expressly depicted but which are obvious variations of the expressly depicted features are expressly incorporated herein by reference.

Figure 1:
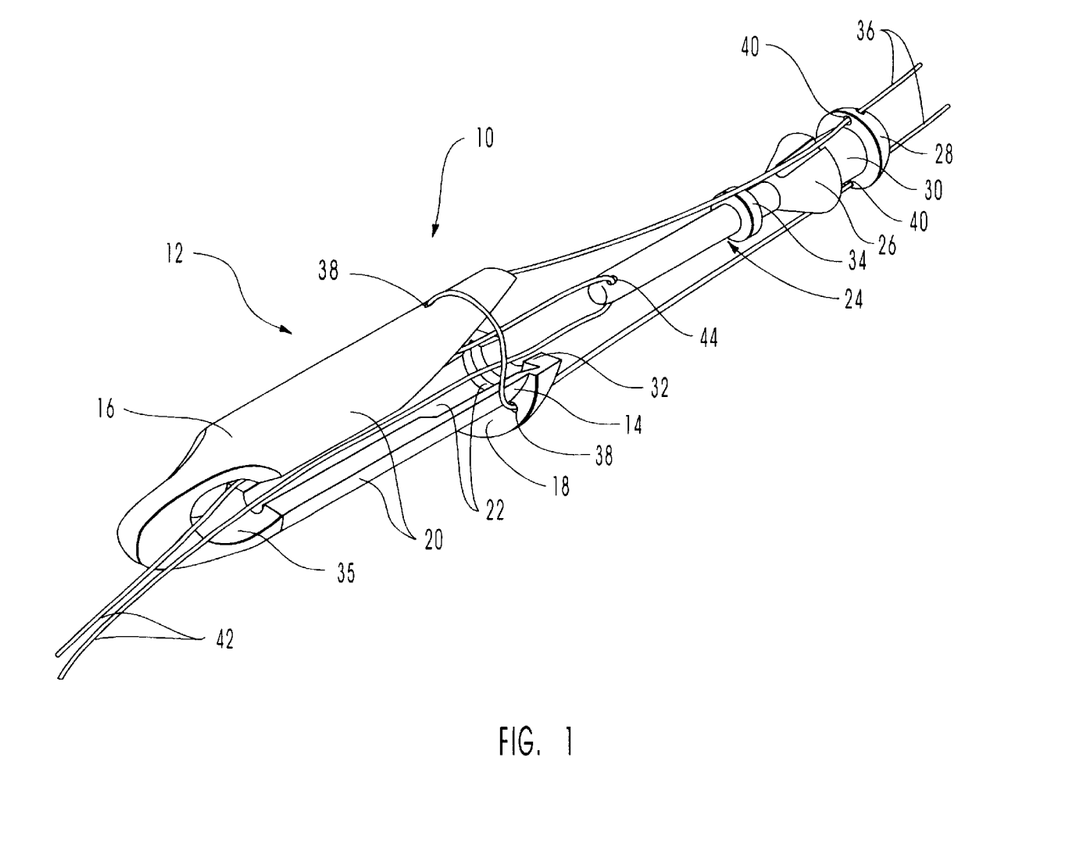
FIG. 1 is an exploded perspective view of an anchor device illustrating a sheath member and an internally fitting slidable pin member having a cam structure thereon.
Figure 3:
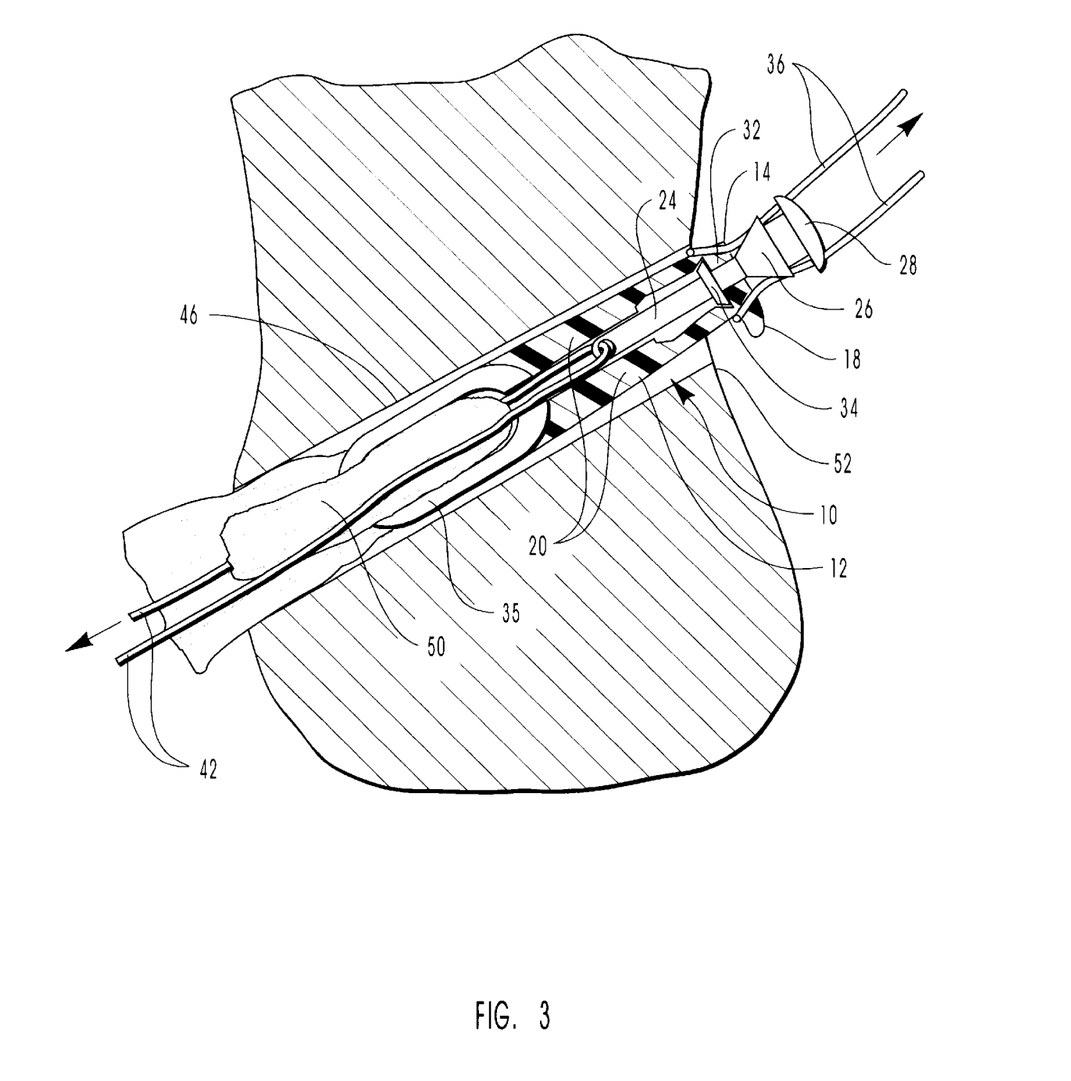
FIG. 3 is a cross-sectional view of the anchor device depicted in FIG. 2 in a semi-deployed state.
Figure 4:
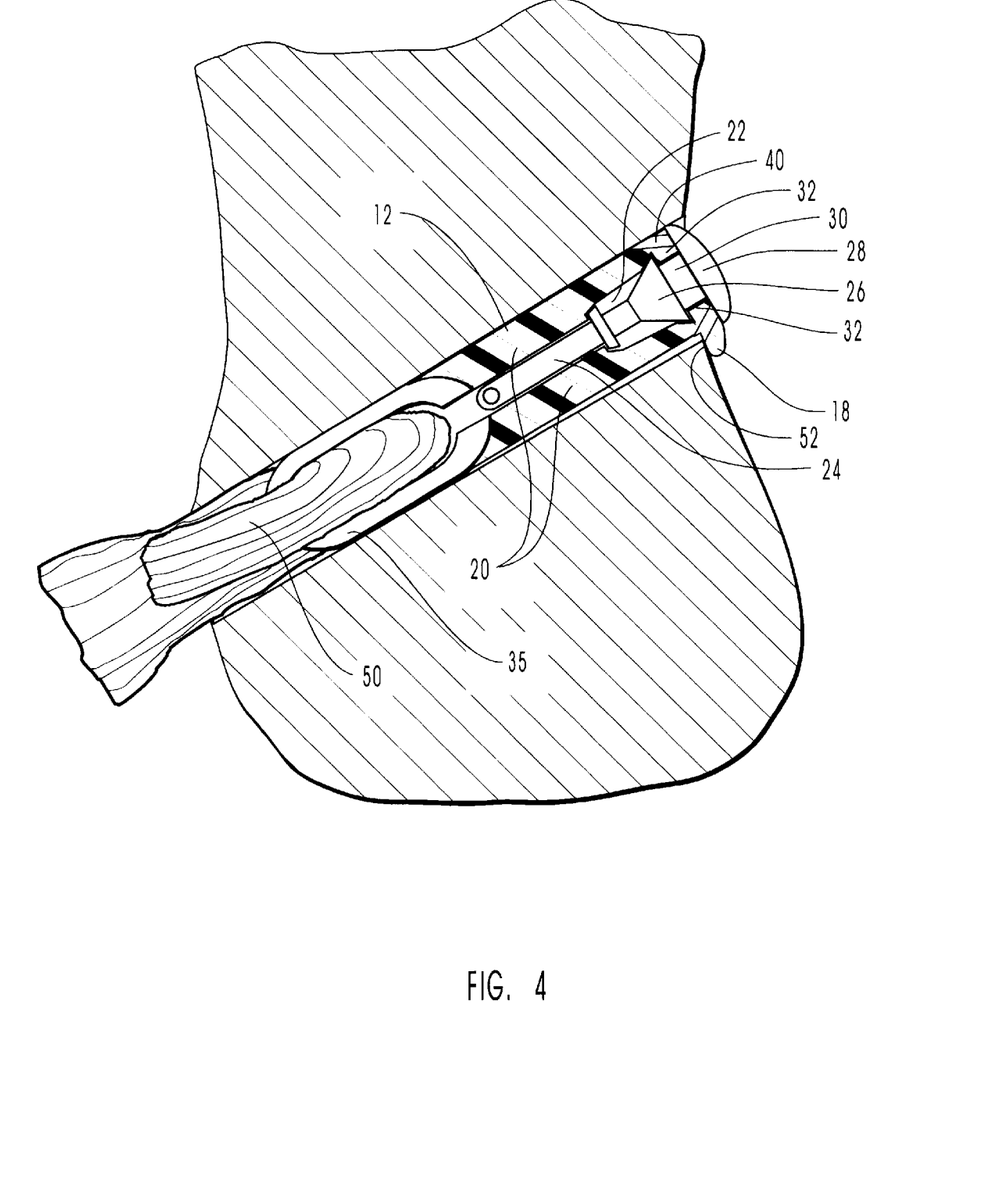
FIG. 4 is a cross-sectional view showing the anchor device depicted in FIGS. 2 and 3 in a fully deployed and locked configuration.

FIG. 1 depicts an anchor device 10 for attaching a bodily tissue to a bone according to the present invention. Anchor device 10 comprises a sheath member 12 including a bone-attachment end 14 and a bodily tissue-attachment end 16. A single bone-attachment lip 18 extends laterally from bone attachment end 14 in order to provide structure for overlapping and engaging a bone surface upon deployment, as discussed hereinbelow. Sheath member 12 is depicted as being slotted longitudinally to form a pair of prongs 20 that terminate at bone-attachment end 14 in order to provide adequate flexibility so that bone-attachment lip 18 can be retracted during insertion of anchor device 10 through a bone tunnel and then extended during deployment (FIGS. 2–4).

Sheath member 12 also includes a central bore or recess 22 configured to receive therein a corresponding pin member 24 having deployment and locking features. Pin member 24 includes a cam member 26, an end dome 28, and a locking recess 30 disposed between cam member 26 and end dome 28. A pair of corresponding locking ridges 32 surrounding central recess 22 at the ends of prongs 20 are configured to mate with locking recess 30 (FIG. 4) in order to lock anchor device 10 in a deployed configuration upon retracting pin member 24 into the central recess 22 of sheath member 12. Pin member 24 also includes a retention ridge 34, which makes abutment with locking ridges 32 in order to prevent pin 24 from inadvertently being withdrawn too far out of sheath member 12 during insertion of anchor device 10 through a bone tunnel.

Bodily tissue-attaching end 16 is configured to include a tissue graft loop 35 in order to provide structure for connecting a bodily tissue to sheath member 12. While tissue graft loop 35 may be preferable in many cases, any bodily tissue attaching structure known in the art may be used to attach a bodily tissue to sheath member 12.

Figure 2:
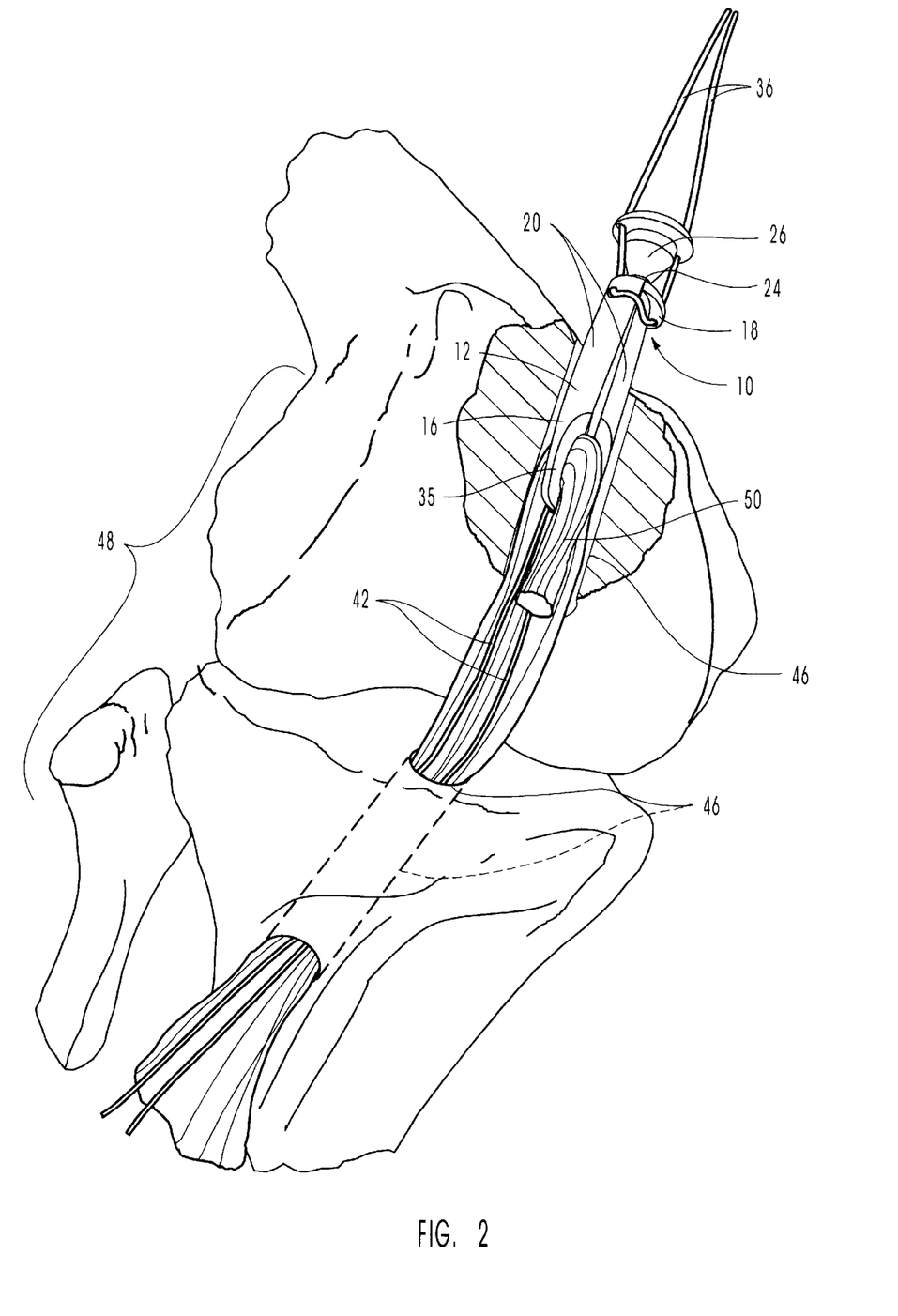
FIG. 2 is a perspective view of the anchor device of FIG. 1, in a non-deployed state, attached to a ligament graft and in the process of being deployed through a bone tunnel.

Attached to bone-attachment end 14 of sheath member 12 is an insertion suture 36, which is used to pull anchor device 10 and an attached bodily tissue through the bone tunnel (FIG. 2). Insertion suture 36 is depicted as being threaded through a pair of attachment holes 38 disposed within bone-attachment end 14 of sheath 12 and through a pair of guide holes 40 within end dome 28. The combination of insertion suture 36 and guide hole 40 assists in properly orienting pin member 24 during insertion and deployment of anchor device 10.

Preferably, insertion suture 36 will comprise a closed loop configuration to prevent inadvertent removal of the suture 36 during insertion and deployment of anchor device 10. This closed-loop configuration in combination with attachment holes 38 provides a reliable connection between insertion suture 36 and sheath member 12, and it also tends to pinch together bone-attachment end 14 and maintain bone-engagement lip 18 in a non-deployed and withdrawn configuration. The closed-loop configuration further allows the suture 36 to be easily withdrawn from the sheath member 12 after insertion and deployment of anchor device 10 by severing the suture 36 and pulling on one of the resulting free ends. The other free end of the suture 36 will allow the suture to follow the suture path and be withdrawn out of the surgical site. Nevertheless, it should be understood that any reliable and removable system of sutures known in the art may be employed within the scope of the invention. In addition, bioabsorbable sutures may be left in the patient in some instances.

Attached to pin member 24 is a deployment suture 42, which is used to retract pin member 24 into the central recess 22 of sheath member 12 in order to deploy and lock anchor device 10 within the bone tunnel. Deployment suture 42 is depicted as being secured to pin member 24 by being threaded through a hole 44 near an end of pin member 24 distal to end dome 28. Deployment suture 42 will also preferably comprise a closed-loop configuration in order to provide a reliable connection between deployment suture 42 and pin member 24 and allow for easy removal of the suture 42 after deployment of the anchor device 10.

Sheath member 12 is preferably made from a resilient material that allows sheath member 12 to be sufficiently flexible so that it can be expanded during deployment to allow the bone-engagement lip 18 to be positioned in an overlapping configuration relative to cortical bone surrounding the exit end of the bone tunnel. In a preferred embodiment, sheath member 12 is manufactured in order that prongs 20 are normally compressed together at bone-engagement end 14 while sheath member 12 is in a relaxed condition. This causes bone-engagement lip 18 to assume a normally retracted configuration during insertion of anchor device 10 through a bone tunnel, which tends to assist in preventing unnecessary and unwanted interference and friction between the bone-engagement lip 18 and the interior wall of the bone tunnel. If sheath member 12 is manufactured in this manner, bone-engagement lip 18 will only expand into the deployed configuration as a result of the camming action provided by cam member 26 upon retracting pin member 24 into the central recess 22 of sheath member 12. Nevertheless, it is certainly within the scope of the invention to manufacture sheath member 12 in other configurations, such as where the prongs 20 assume a normally spread or expanded configuration while sheath member 12 is in a relaxed state.

Anchor device 10 is used as follows to attach a bodily tissue to a bone. First an appropriate bone tunnel is prepared through the bone to which it is desired to attach the bodily. As depicted in FIG. 2, two bone tunnels 46 are formed within the two bones of a joint 48. Bone-tunnel preparation means and techniques known to those of ordinary skill may be used to prepare the bone tunnels 46. A detailed description of preferred methods and apparatus for preparing a bone tunnel preparatory to implantation of a graft tissue such as a ligament graft is set forth in U.S. Pat. Nos. 5,139,520 and 5,374,269 to Rosenberg. For purposes of disclosing preferred methods and apparatus for preparing a bone tunnel, the foregoing patents are incorporated herein by specific reference.

After preparing the appropriate bone tunnel(s) 46, a bodily tissue 50 is looped through tissue graft loop 35 of bodily tissue-attachment end 16 of sheath member 12, or may be attached using any appropriate means known in the art. Using insertion sutures 36, anchor device 10 and the attached bodily tissue 50 are pulled through the bone tunnel (s) 46 as depicted in FIG. 2. During insertion, bone-engagement lip 18 is able to retract into a non-deployed position in order to allow insertion of anchor device 10 through the bone tunnel 46. Pin member 24 is partially withdrawn from sheath member 12 in order that the cam member 26 does not substantially urge apart the prongs 20 of sheath member 12. Insertion suture 36, which passes through guide hole 40 of pin member 24, assists in maintaining pin member 24 in an appropriate position during insertion and later during deployment. Retention ridge 34 will abut locking ridges 28 of sheath member 12 as needed in order to prevent pin 24 from inadvertently being withdrawn too far out of sheath member 12 during insertion of anchor device 10 through the bone tunnel (FIG. 3).

FIG. 3 shows a cross-sectional view of the combination of anchor device 10 and bodily tissue 50 inserted through bone tunnel 46 and depicts how the various structural features of sheath member 12 and pin member 24 work together to maintain the anchor device in a desired conformation during insertion. After bone-engagement end 14 of sheath member 12 has emerged sufficiently from the exit opening of the bone tunnel 46, anchor device 10 may be deployed and locked in a deployed configuration. FIG. 3 more clearly shows how cam member 26 will, upon retracting pin member 24 into central recess 22 of sheath member 12, urge prongs 20 at bone-engagement end 14 apart by pushing against locking ridges 32 in order to deploy anchor device 10 and cause bone-engagement lip 18 to extend over a bone surface 52 adjacent the exit opening of the bone tunnel.

FIG. 4 illustrates the anchor device 10 depicted in FIGS. 2 and 3 after being deployed and locked in the deployed condition and after removing the sutures. Deployment and locking of anchor device 10 is carried out by applying sufficient tension to deployment suture 42 (FIG. 3) to cause pin member 24 to be withdrawn into central bore 22 of sheath member 12, while applying a counter tension to insertion suture 36 in order to maintain the bone-engagement end 14 of sheath member 12 outside the exit hole of the bone tunnel 46. Care should be taken to avoid inadvertently allowing anchor device 10 to be withdrawn back into the bone tunnel 46 to an extent that would permit bone-engagement lip 18 to be deployed and extended outwardly within the bone tunnel 46, unless the anchor device has been modified to provide for deployment and bone attachment in this manner.

The opposing tensile forces applied by insertion suture 36 and deployment suture 42 cause cam member 26 to spread apart prongs 20 of sheath member 12, after which locking ridges 32 mate with locking recess 30 of pin member 24. Mating of ridges 32 and locking recess 30 causes anchor device 10 to be locked in the deployed configuration and prevents inadvertent de-deployment of anchor device 10. In addition, mating of ridges 32 and locking recess 30 provides tactile confirmation that anchor device 10 has been properly deployed and locked in the deployed state. After reliably deploying and locking anchor device 10 in the deployed position, the surgeon can remove the sutures by cutting and pulling on one of the free ends of each suture.

It should be understood that the foregoing method for anchoring a bodily tissue within a bone tunnel may be performed either before or after securing the other end of the bodily tissue. In either case, it is preferable for the bodily tissue to exert tension on the anchor device upon completing the reconstructive surgery in order to more reliably maintain the anchor device and graft bodily tissue in a substantially rigid and secure configuration. Maintaining the bodily tissue in a rigid configuration relative to the bone tunnel promotes earlier biological adhesion between the bodily tissue and wall of the bone tunnel compared to less rigid attachments.

In a preferred embodiment, the anchor device of the invention will further include means for displacing the bodily tissue from the center of the bone tunnel and urging the bodily tissue circumferentially against the walls of the bone tunnel. Accordingly, alternative embodiments of anchor devices according to the invention are illustrated in FIGS. 5–8 as having a substantially cylindrical extension projecting from the bodily tissue attachment end of the sheath member.

Figure 5:
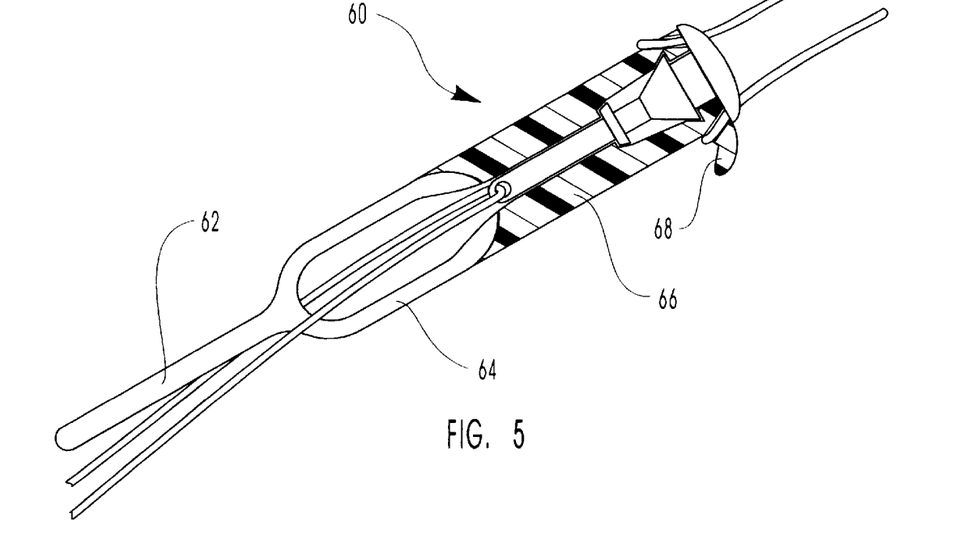
FIG. 5 is cross-sectional view of another embodiment of an anchor device having a substantially cylindrical extension projecting from the bodily tissue attachment end.

FIG. 5 depicts an alternative embodiment of an anchor device 60 that is similar to anchor device 10 of FIGS. 1–4, except that anchor device 60 further includes a substantially cylindrical extension 62 projecting from a bodily tissue-attachment end 64 of a sheath member 66. Although extension 62 is shown to be substantially cylindrical, it should be understood that extension 62 can have any cross-sectional shape so long as it provides substantially the same function as extension 62, which is depicted as being substantially cylindrical. A preferred function of extension 62 has been heretofore set forth, although any other inherent or obvious function could certainly provide one of ordinary skill in the art with motivation to modify extension 62 in a manner that provides any of these other functions.

Anchor device 60, as depicted in FIG. 5, also differs from anchor device 10 of FIGS. 1–4 in that a bone-engagement lip 68 having a more acute angle relative to sheath member 66 is depicted. In fact, the bone-engagement lip of the anchor devices of the present invention may be oriented at any appropriate angle. In general, it is preferable to provide a bone-engagement lip having an angle which corresponds to the angle of the bone tunnel.

In still other cases, it may be preferable for the bone-engagement lip to be bent or hooked to provide any desired engagement with the bone surface adjacent the exit opening of the bone tunnel. For example, bone-engagement lip may be configured and angled to maximize the surface contact with the bone surface. Alternatively, the bone-engagement lip may be hooked or otherwise configured in order to penetrate into the bone surface if possible. The bone-engagement lip may be configured to flex upon contacting the bone surface in order to increase tension on the bodily tissue graft. In short, virtually any bone-engagement lip configuration or other means for overlapping and engaging the bone surface may be utilized within the scope of the invention.

Figure 6:
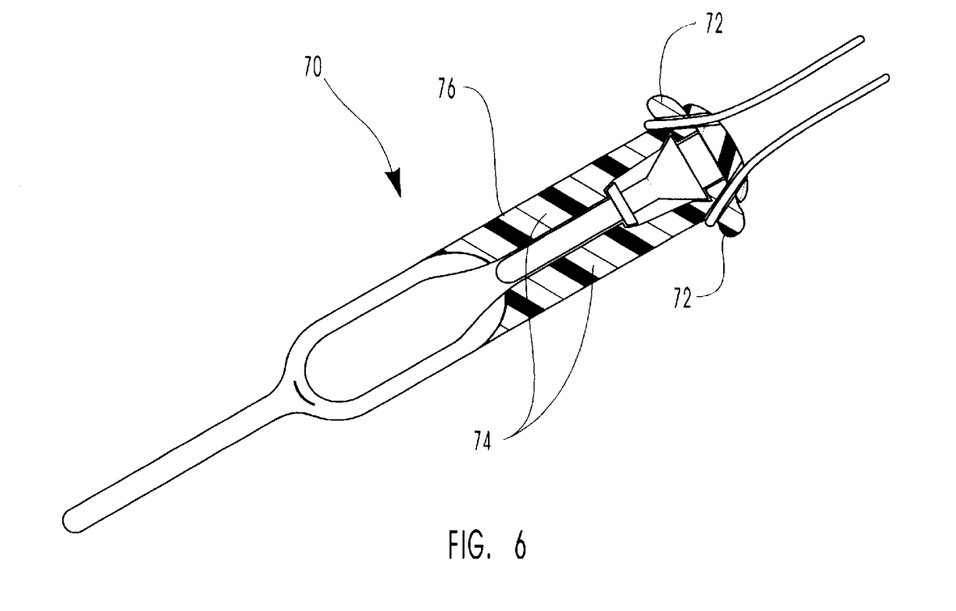
FIG. 6 is a cross-sectional view of an alternative anchor device having a double bone-engagement lip configuration.

FIG. 6 depicts an alternative anchor device 70 that is similar to anchor device 60 of FIG. 5, except that anchor device 70 has a double-lip configuration. In particular, anchor device 70 includes a pair of bone-engagement lips 72 extending laterally from two corresponding prongs 74 of sheath member 76. An advantage of a double-lip configuration is that it ensures a more reliable engagement with surrounding cortical bone in the case where the geometry and quality of the bone surface surrounding the exit opening of the bone tunnel are imperfect, highly variable, or uncertain. In general, a double-lip configuration works better in cases where the bone tunnel is relatively perpendicular relative to the bone axis. In the case where the bone tunnel is oriented at a different angle, e.g. 45°, a double-lip configuration will generally result in the bone-engagement end of the sheath member being extended from the bone surface to a significant degree. In addition, only one of the bone-engagement lips will actually contact the bone surface in many cases, thereby rendering the other bone-engagement lip superfluous.

Bone tunnels formed during cruciate reconstruction surgery typically have angles at the exit opening of the tunnel between about 45–60° relative to the plane of the bone surface. It would therefore be advantageous to provide an anchor device having a corresponding bone-engagement lip angle. Nevertheless, so long as the bone-engagement lip is able to reliably overlap and engage the bone surface adjacent the exit opening of the bone tunnel, the actual angle of the bone-engagement lip is not normally critical. Moreover, it would certainly be within the scope of the invention to provide an anchor device having a bone-engagement lip that had a self-adjusting angle (not shown) in order to maximize surface contact between the bone-engagement lip and the bone surface. It would also be within the scope of the invention to provide a bone-engagement lip that had a self-adjusting angle of rotation (not shown) in order to provide a proper angular orientation of the bone-engagement lip during insertion and deployment.

Figure 7:
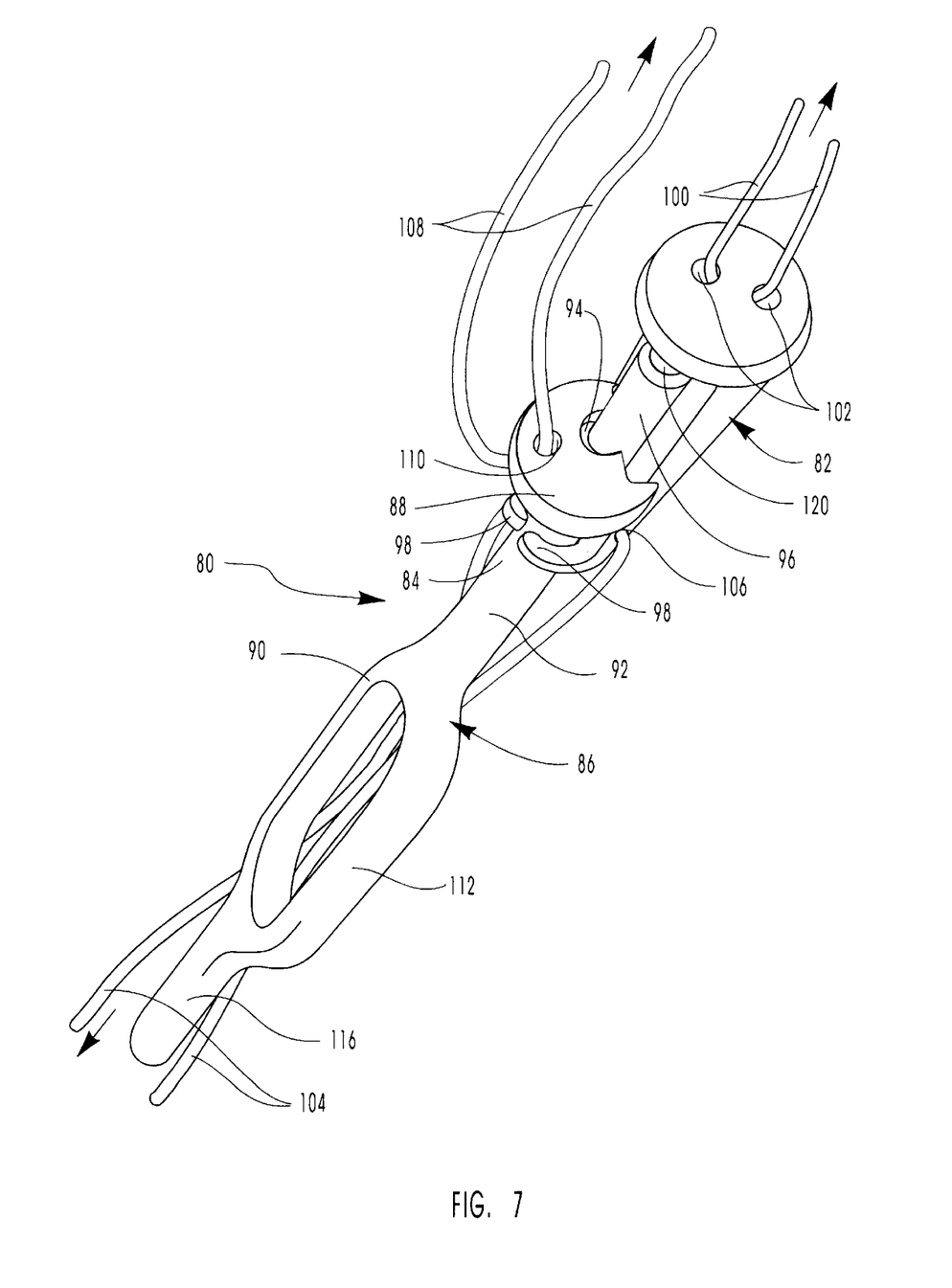
FIG. 7 is a perspective view of an alternative anchor device having a sliding wedge member is a non-deployed state.
Figure 8:
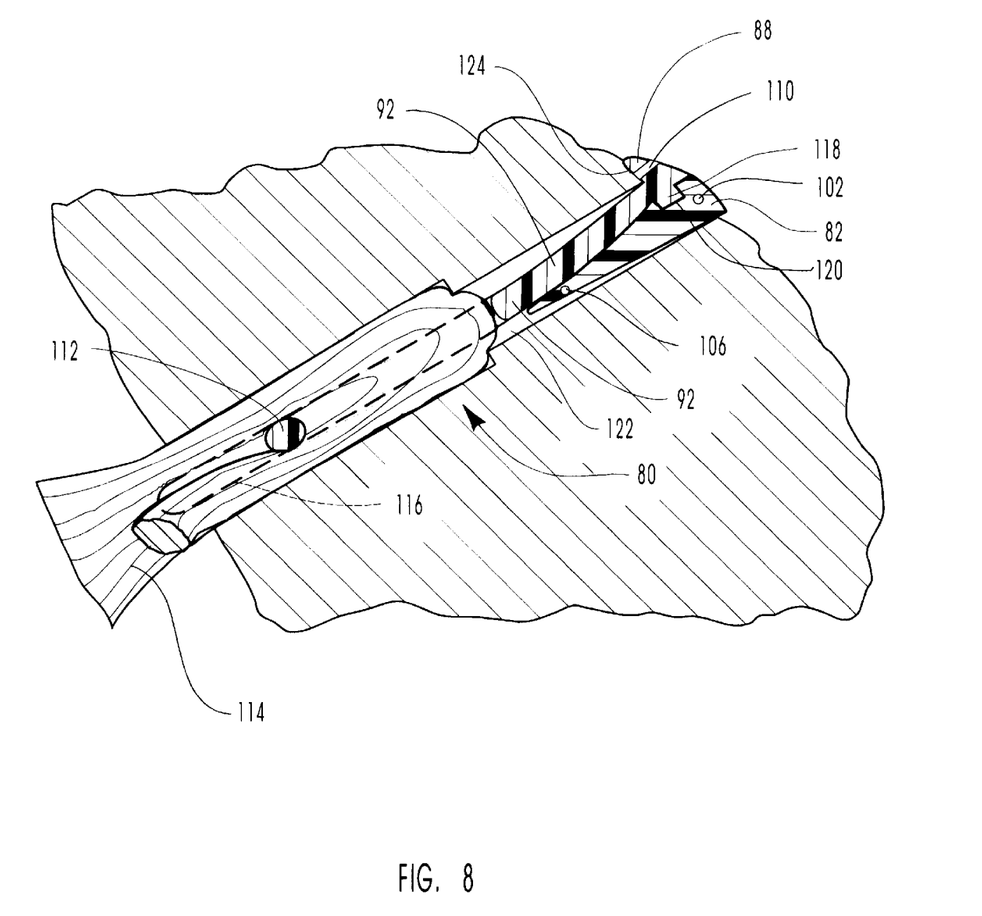
FIG. 8 is a cross-sectional view of the anchor device of FIG. 7 attached to a ligament graft and deployed within a bone tunnel in a locked configuration.

FIGS. 7 and 8 depict another preferred embodiment of an anchor device according to the present invention. FIG. 7 illustrates an anchor device 80 that differs from the anchor devices depicted in FIGS. 1–6 mainly in the type of cam member that is utilized to deploy and lock the anchor device 80. Instead of the internally positioned pin member depicted in FIGS. 1–6, anchor device 80 includes a sliding wedge member 82 disposed adjacent a bone-engagement end 84 of a sheath member 86. However, the principles involved in deployment and locking of anchor device 80 are substantially the same as in the other illustrative anchor devices disclosed herein. In fact, virtually any combination of sheath member and slidable cam member can be used so long as they provide for deployment and/or locking of the anchor device in the manner described in the specification.

Bone-engagement end 84 is depicted as including a single bone-engagement lip 88 extending laterally from bone-engagement end 84. Bone-engagement end 84 is attached to a bodily tissue-attachment end 90 by means of shaft 92. The bone-engagement end 84 of shaft 92 includes a key way 94 that provides means for slidably engaging a corresponding key ridge 96 disposed on wedge member 82. The slidable engagement between key way 94 and key ridge 96 provides for approximate parallel alignment of wedge member 82 and sheath member 86. A pair of stops 98 disposed at a lower end of wedge member will make abutment with the underside of bone-engagement lip 88 as wedge member 82 is withdrawn from sheath member 86 in order to prevent complete separation of wedge member 82 from sheath member 86 and thereby maintain the slidable connection therebetween. It should be understood that key way 94 and key ridge 96 could be reversed so that wedge member 82 includes the key way and sheath member 86 includes the key ridge. Moreover, any stop feature that prevents wedge member 82 from completely detaching from sheath member 86 may be employed.

An insertion suture 100 is connected to an upper end of wedge member 82 through connection holes 102. A deployment suture 104 is connected to a lower end of wedge member 82 through a hole 106. A counter-tensioning suture 108 is connected to bone-engagement end 84 of sheath member 86 through a hole 110.

Bodily tissue-attachment end 90 is depicted as including a loop member 112 through which one or more strands of bodily tissue, such as a ham string graft 114, can be threaded as described in other embodiments. In addition, a spacing extension 116 projects longitudinally from the tissue-attachment end 90 to provide the function of enhanced tissue adhesion as described hereinabove.

In use, the combination of anchor device 80 and ham string graft 114 is pulled through a bone tunnel by pulling on insertion suture 100, which directly applies a tensile force to wedge member 82. Upon pulling wedge member 82 using insertion suture 100, stops 98 at the lower end of wedge member 82 will make abutment with the underside of bone-engagement lip 88, which thereby transfers the tensile force exerted by insertion suture 100 from wedge member 82 to sheath member 86, thereby pulling the entire anchor device 80 and ham string graft 114 through the bone tunnel.

After pulling anchor device 80 through the bone tunnel so that bone-engagement lip 88 emerges from the exit opening of the bone tunnel, the anchor device is deployed by simultaneously pulling on deployment suture 104 and counter-tension suture 108 to cause relative movement between wedge member 82 and sheath member 86. This, in turn, causes wedge member 82 to be pulled into the exit opening of the bone tunnel, which causes bone-engagement lip 88 to be extended laterally over the bone surface surrounding the exit opening as the wider upper portion of wedge member 82 is positioned adjacent bone-engagement end 84 of sheath member 86.

Upon deployment, a locking ridge 118, disposed on bone-engagement end 84 and projecting rearwardly relative to bone-engagement lip 88, will mate with a corresponding mating recess 120 within wedge member 82. Locking ridge 118 and mating recess 120 work together to maintain wedge member 82 and sheath member 86 locked together in the deployed configuration. In addition, locking ridge 118 and mating recess 120 will snap together during deployment and locking of anchor device 80 in the deployed position to thereby provide tactile confirmation that anchor device 80 has been properly deployed and locked in the deployed position.

FIG. 8 illustrates anchor device 80 attached to ham string graft 114 and in a deployed and locked condition within a bone tunnel 122. Spacing extension 116 is shown to occupy the center of the bone tunnel 122 in the region below bodily tissue-attachment end 90 in order to urge the ham string graft 114 against the wall of bone tunnel 122. Wedge member 82 is depicted as causing bone-engagement lip 88 to be remain laterally extended over adjacent bone surface 124 surrounding bone tunnel 122 in the final deployed state. Locking ridge 118 and mating recess 120 interlock together to maintain wedge member 82 and sheath member 86 locked in the deployed configuration.

FIG. 8 also depicts bone tunnel 122 as having a specially prepared bore configuration having a larger diameter bore at the rearward end compared to the bore diameter at the forward or exit end. The diameter of the forward end is shown as being large enough to permit passage therethrough of bone-engagement end 84 but not the portion of loop member 96 through which ham string graft 114 is threaded. Because the ham string graft 114 makes abutment with the bone tunnel wall at the point where it narrows to the smaller diameter bore, bone tunnel configurations such as those depicted in FIG. 8 can be used to advantageously prevent excessive insertion of the anchor device and bodily through the bone tunnel. This stopping point provided by this bone tunnel configuration thus provides means for limiting the amount of insertion of the anchor device and bodily tissue through the bone tunnel. This can assist the surgeon in properly positioning the anchor device prior to deployment and locking.

Although the foregoing embodiments depict a single locking ridge disposed on a bone-engagement end of a sheath member, which corresponds to and mates with a locking recess within the illustrative camming means, other configurations are certainly within the scope of the invention. For example, the interlocking components could be reversed in order to provide a sheath member having a locking recess and a camming means having a corresponding locking ridge (not shown). Alternatively, various combinations of locking ridges and recesses could be provided on both the sheath member and the camming means (not shown) so long as they provided the desired locking function and/or tactile confirmation of deployment and locking.

The sheath members depicted in FIGS. 1–8 and described in the accompanying discussion are given by way of example. The term "sheath member" should be broadly interpreted to include any structure that is capable of having a bodily tissue attached thereto at one end and which is capable of overlapping, engaging, or otherwise capable of being rigidly secured to a bone in a manner similar to how the illustrative sheath members are able to anchor a bodily tissue within a bone tunnel. Any of the sheath members described in the specification and also all functionally equivalent variants comprise "sheath means for attaching a bodily tissue to a bone".

Likewise, cam member 26 attached to the pin member 24 and the slidable wedge member 82 depicted in FIGS. 1–8 and described in the accompanying discussion are given by way of example. The term "cam member" should be broadly interpreted to include any structure that is capable of providing the same functions as cam member 26 and slidable wedge member 82, including but not limited to, the ability to cause a bone-engagement lip or other bone-engagement means of a sheath member to overlap a bone surface at the exit end of a bone tunnel by sliding the structure relative to the sheath member. The cam member 26 and wedge member 82, as well as also all functionally equivalent variants thereof, comprise "camming means".

The single and double lipped bone-engagement lips depicted in the drawings and described herein are given by way of example only. Any structure attached to the sheath member that is capable of overlapping, engaging, or otherwise preventing pull-out of a sheath from a bone tunnel after deployment should be considered to fall within the scope of the term "bone-engagement means".

The interlocking features described above comprising a ridge and recess that snap together during deployment to provide tactile confirmation that the anchor device has been properly deployed and locked in the deployed state are but one illustration of "signaling means". Any mechanical, electronic, or visual indication of successful deployment and locking may comprise signaling means. The signaling means may be as simple as a suture having a visible marking that is attached to the camming means and which allows for visual monitoring of relative movement between the camming means and the sheath means during deployment.

The anchor devices manufactured according to the invention preferably comprise a bioabsorbable material, which can be absorbed over time and replaced with living tissue. The sheath member, cam member and sutures may all be advantageously made of a bioabsorbable material. An example of a preferred bioabsorbable material that could be used to manufacture the anchor devices of the present invention is a poly-l-lactic acid polymer, also known as "PLLA". Other bioabsorbable materials known in the art are described in detail in U.S. Pat. No. 4,643,734 to Lin. For purposes of disclosing bioabsorbable materials, the foregoing patent is incorporated herein by specific reference. Notwithstanding, it should be understood that using a bioabsorbable anchor device is not critical for obtaining a strong biological bond between the graft bodily tissue and the bone.

In conclusion, the present invention provides a simple, more easily deployed anchor device that can securely attach a bodily tissue such as a replacement ligament graft to a bone.

The present invention also provides an anchor device that can be reliably deployed while minimizing the invasiveness of the surgery, particularly the number of incisions that have to be made by the surgeon for proper deployment.

In addition, the present invention discloses an anchor device that includes a mechanism that provides a discernable signal or means to indicate when the anchor device has been successfully deployed and securely engaged within the bone.

The present invention further provides an anchor device that allows for broad surface contact between the graft tissue and the inner surface of the bone tunnel in order increase the biological bond and provide a stronger, more reliable connection with the bone.

The present invention also provides an anchor device that can be easily molded from a bio-absorbable material.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An anchor device for securing a bodily tissue within a pre-prepared bone tunnel comprising:

sheath means for attaching a bodily tissue to a bone, said sheath means being configured and sized to pass through a pre-prepared bone tunnel and including a bone-engagement end and a bodily tissue attachment end, the bone-engagement end having bone-engagement means for selectively overlapping and engaging a bone surface adjacent an exit opening of the bone tunnel, the bodily tissue attachment end having tissue securing means for securing a bodily tissue to said sheath means; and camming means, in slidable contact with said sheath means during deployment of said anchor device, for selectively urging said bone-engagement means to overlap and engage the bone surface adjacent the exit opening of the bone tunnel, said camming means being configured so as to remain part of said anchor device upon deployment.

2. An anchor device as defined in claim 1, wherein said sheath means comprises a sheath member in which said bone-engagement end is able to assume different positions in response to movement of said camming means in relation to said bone-engagement end in order to thereby selectively position said bone-engagement means between a non-deployed position, in which said bone-engagement means is withdrawn inwardly to allow passage of the anchor device through the bone tunnel, and a deployed position, in which said bone-engagement means is extended outwardly to allow for overlap and engagement of the bone surface.

3. An anchor device as defined in claim 2, wherein said bone-engagement means comprises a single bone-engagement lip extending laterally from said bone-engagement end.

4. An anchor device as defined in claim 3, wherein said bone-engagement lip is oriented at an angle that provides for increased surface contact with the bone surface upon deployment of said anchor device.

5. An anchor device as defined in claim 2, wherein said bone-engagement means comprises a plurality of bone-engagement lips extending laterally from said bone-engagement end.

6. An anchor device as defined in claim 1, wherein said tissue securing means comprises a loop member.

7. An anchor device as defined in claim 1, wherein said camming means comprises a pin member slidably disposed within an interior recess of said sheath means and having a cam structure disposed thereon for selectively positioning said sheath means between a non-deployed position and a deployed position upon slidably moving said pin member relative to said sheath means.

8. An anchor device as defined in claim 1, wherein said camming means comprises a wedge member slidably disposed adjacent said bone-engagement end of said sheath means and capable of selectively positioning said sheath means between a non-deployed position and a deployed position upon slidably moving said wedge member relative to said sheath means.

9. An anchor device as defined in claim 8, further including means for maintaining slidable engagement between said wedge member and said sheath means.

10. An anchor device as defined in claim 1, further including locking means for locking together said sheath means and said camming means upon deployment of the anchor device in order to reliably maintain the anchor device in a deployed state.

11. An anchor device as defined in claim 10, wherein said locking means comprises a ridge disposed on at least one of said sheath means and said camming means and configured to mate with a corresponding recess in at least one of said camming means and said sheath means upon deployment of the anchor device.

12. An anchor device as defined in claim 11, wherein said ridge and said recess, upon mating, provide a tactile indication that the anchor device has been properly deployed and locked in the deployed position.

13. An anchor device as defined in claim 1, further including signaling means for indicating when the anchor device has been properly deployed and locked in the deployed position.

14. An anchor device as defined in claim 13, wherein said signaling means comprises a ridge disposed on at least one of said sheath means and said camming means and configured to mate with a corresponding recess in at least one of said camming means and said sheath means during deployment of the anchor device.

15. An anchor device as defined in claim 13, wherein said signaling means comprises a suture attached to said camming means and including a visible marking that allows for visual monitoring of relative movement between said camming means and said sheath means during deployment.

16. An anchor device as defined in claim 1, wherein said sheath means is configured to assume a normally non-deployed position while in a relaxed condition in which said bone-engagement means is in a withdrawn position to facilitate insertion of the anchor device through the bone tunnel.

17. An anchor device as defined in claim 1, further including an extension projecting from said bodily tissue attachment end of said sheath means for providing increased surface-area contact between the bodily tissue and the bone tunnel.

18. An anchor device as defined in claim 1, further comprising an insertion suture connected to said sheath means for pulling the anchor device through a bone tunnel and a deployment suture connected to the camming means that, upon pulling with sufficient force, causes said camming means to urge said bone-engagement means in an overlapped and engaged configuration relative to the bone surface.

19. An anchor device for securing a bodily tissue within a pre-prepared bone tunnel comprising:

a sheath member configured and sized to pass through a pre-prepared bone tunnel and including a bone-engagement end and a bodily tissue attachment end, said bone-engagement end including at least one bone-engagement lip extending laterally therefrom and being moveable in order that said bone-engagement lip can be selectively positioned between a non-deployed position, in which said bone-engagement lip is withdrawn inwardly to allow passage of the anchor device through the bone tunnel, and a deployed position, in which said bone-engagement lip is extended outwardly to allow for overlap and engagement of the bone surface by said bone-engagement lip, the bodily tissue attachment end being capable of having a bodily tissue secured thereto; and a cam member in slidable contact with said sheath member during deployment of said anchor device and configured so as to selectively urge said bone-engagement lip from a withdrawn, non-deployed position to an extended, deployed position in which said bone-engagement lip at least partially overlaps the bone surface upon sliding said cam member in relation to said sheath member.

20. An anchor device as defined in claim 19, wherein said bone-engagement lip is oriented at an angle that provides for increased surface contact with the bone surface upon deployment of said anchor device.

21. An anchor device as defined in claim 19, said bodily tissue securing end further including a loop member through which a bodily tissue can be threaded.

22. An anchor device as defined in claim 19, said cam member comprising part of a pin member that is slidably disposed within an interior recess of said sheath member.

23. An anchor device as defined in claim 22, said pin member further including a ridge that makes abutment with a corresponding surface of said sheath member upon partially withdrawing said pin member from said sheath member while said sheath member is in a withdrawn and non-deployed position.

24. An anchor device as defined in claim 22, further comprising an insertion suture connected to said sheath member for pulling the anchor device through a bone tunnel and a deployment suture connected to said pin member that, upon pulling with sufficient tensile force against tension provided by said insertion suture, causes said cam member to urge said bone-engagement lip in the deployed position in which said lip bone-engagement overlaps and engages the bone surface.

25. An anchor device as defined in claim 19, said cam member comprising a wedge structure slidably disposed adjacent said bone-engagement end of said sheath member and configured to selectively position said sheath member between a withdrawn, non-deployed position and an extended, deployed position upon slidably moving said wedge member relative to said sheath member.

26. An anchor device as defined in claim 25, wherein one of said wedge structure and said sheath member further includes a key ridge that slidably mates with a corresponding key way within another of said wedge structure and said sheath member.

27. An anchor device as defined in claim 26, wherein said wedge structure further includes a stop which assists in preventing said wedge structure from being completely detached from said sheath member.

28. An anchor device as defined in claim 27, further comprising an insertion suture connected to said wedge member for pulling the anchor device through a bone tunnel, a deployment suture connected to said sheath member, and a counter-tensioning suture attached to said sheath member.

29. An anchor device as defined in claim 19, at least one of said cam member and said sheath member further including a recess configured to mate with a corresponding ridge on at least one of said sheath member and said cam member upon deployment of the anchor device in order to lock the anchor device in the deployed position.

30. An anchor device as defined in claim 29, wherein said recess and said ridge, upon mating, provide the surgeon with a tactile indication that the anchor device has been properly deployed and locked in the deployed position.

31. An anchor device as defined in claim 19, wherein said sheath member is configured such that said bone-engagement lip is initially in a withdrawn position while said sheath member is in a relaxed condition in order to facilitate insertion of the anchor device through the bone tunnel.

32. An anchor device as defined in claim 19, further including a substantially cylindrical extension projecting from said bodily tissue attachment end of said sheath member.

33. An anchor device for securing a bodily tissue within a pre-prepared bone tunnel comprising:

a sheath member configured and sized to pass through a pre-prepared bone tunnel and including a bone-engagement end and a bodily tissue attachment end, said bone-engagement end including at least one bone-engagement lip extending laterally therefrom and being moveable in order that said bone-engagement lip can be selectively positioned between a non-deployed position, in which said bone-engagement lip is withdrawn inwardly to allow passage of the anchor device through the bone tunnel, and a deployed position, in which said bone-engagement lip is extended outwardly to allow for overlap and engagement of the bone surface by said bone-engagement lip, the bodily tissue attachment end being capable of having a bodily tissue secured thereto;

a cam member in slidable contact with said sheath member during deployment of said anchor device and configured so as to selectively urge said bone-engagement lip from a withdrawn, non-deployed position to an extended, deployed position in which said bone-engagement lip at least partially overlaps the bone surface upon sliding said cam member relative to said sheath member;

a locking mechanism comprising a ridge disposed on one of said sheath member and said cam member and a corresponding recess within the other of said cam member and said sheath member, wherein upon mating of said ridge and said recess said sheath member and said cam member are retained in a substantially fixed position in relation to each other, the mating of said ridge and said recess also providing a tactile signal that said anchor device has been properly deployed and locked in the deployed position;

an insertion suture connected to said sheath member for pulling the anchor device through a bone tunnel; and a deployment suture communicating with said cam member that, upon pulling with sufficient force, causes said cam member to urge said bone-engagement lip in the deployed position in which said lip bone-engagement at least partially overlaps and engages the bone surface.

34. An anchor device as defined in claim 33, said cam structure being selected from the group consisting of a cam structure attached to an elongate pin member and a sliding wedge member.

35. A method for attaching a bodily tissue to a bone comprising the steps of:

preparing a bone tunnel having a desired diameter through the bone;

inserting an anchor device secured to a bodily tissue through the bone tunnel by means of an insertion suture until a forward bone-engagement end of said anchor device emerges from an exit opening of said bone tunnel; and deploying said anchor device by pulling a deployment suture with sufficient force to enable a cam structure slidably disposed relative to said bone-engagement end to urge a bone-engagement lip disposed on said bone-engagement end to at least partially overlap a bone surface adjacent said exit opening of said bone tunnel.

36. A method for attaching a bodily tissue to a bone as defined in claim 35, wherein only a single incision through a patient's flesh is made in order to carry out the preparing, inserting and deploying steps.

37. A method for attaching a bodily tissue to a bone as defined in claim 35, the bone tunnel having a forward portion proximal to the exit opening and a rearward portion distal to the exit opening, wherein the forward portion has a reduced bore width compared to the bore width of the rearward portion, which limits how far the anchor device can be inserted through said bone tunnel during the insertion step.

38. A method for attaching a bodily tissue to a bone as defined in claim 35, further including the step of attaching the bodily tissue to the anchor device by looping the bodily tissue through a loop member of the anchor device.

39. A method for attaching a bodily tissue to a bone as defined in claim 35, wherein the deploying step further results in said anchor device being locked in the deployed state such that said bone-engagement lip is locked in the bone-overlapping position relative to the bone surface.

40. A method for attaching a bodily tissue to a bone as defined in claim 39, wherein the deploying step further results in a tactile confirmation that the anchor device has been deployed and locked in the deployed condition.

\* \* \* \* \*

UNITED STATES PATENT AND TRADEMARK OFFICE
CERTIFICATE OF CORRECTION

PATENT NO. : 5,964,764
DATED : Oct. 12, 1999
INVENTOR(S) : Hugh S. West, Jr.; John R. West It is certified that error appears in the above-identified patent and that said Letters Patent are hereby corrected as shown below:

Cover Page, in the Abstract, at line 16, change "bond" to --bone--

Col. 1, line 35, after "surgical" change "stables" to --staples--

Col. 1, line 50, before "made" insert --be--

Col. 3, line 63, after "is" change "define" to --defined--

Col. 5, line 35, after "attached" delete "the"

Col. 6, line 9, after "device" change "include" to --includes--

Col. 6, line 29, after "order" insert --to--

Col. 10, line 43, after "bodily" insert --tissue--

Col. 11, line 4, after "ridges" change "28" to --32--

Col. 11, line 28, after "central" change "bore" to --recess--

Col. 14, line 50, after "member" change "96" to --112--

Col. 15, line 59, change "poly-l-lactic" to --poly-/-lactic--

UNITED STATES PATENT AND TRADEMARK OFFICE
CERTIFICATE OF CORRECTION

PATENT NO. : 5,964,764
DATED : Oct. 12, 1999
INVENTOR(S) : Hugh S. West, Jr; John R. West It is certified that error appears in the above-indentified patent and that said Letters Patent is hereby corrected as shown below:

Column 10, line 43, after "bodily" insert --to--.
Column 11, line 4, after "ridges" change "28" to --32--.
Column 11, line 28, after "central" change "bore" to --recess--.
Column 14, line 50, after "member" change "96" to --112--.
Column 15, line 59, change "poly-1-lactic" to --poly-/-lactic --.

Signed and Sealed this

Third Day of April, 2001

Attest:

NICHOLAS P. GODICI

Attesting Officer    Acting Director of the United States Patent and Trademark Office